US00PP24337P3

(12) United States Plant Patent
Danziger

(10) Patent No.: US PP24,337 P3
(45) Date of Patent: Mar. 25, 2014

(54) ***LOBULARIA* PLANT NAMED 'DLOBU2'**

(50) Latin Name: *Lobularia maritima*
Varietal Denomination: DLOBU2

(75) Inventor: Gavriel Danziger, Moshav Mishmar Hashiva (IL)

(73) Assignee: Danziger 'Dan' Flower Farm (IL)

( * ) Notice: Subject to any disclaimer, the term of this patent is extended or adjusted under 35 U.S.C. 154(b) by 148 days.

(21) Appl. No.: 13/385,908

(22) Filed: Mar. 12, 2012

(65) Prior Publication Data

US 2013/0239276 P1 Sep. 12, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — June Hwu
*Assistant Examiner* — Louanne Krawczewicz Myers
(74) *Attorney, Agent, or Firm* — Cassandra Bright

(57) ABSTRACT

A new and distinct *Lobularia* cultivar named 'DLOBU2' is disclosed, characterized by a dense inflorescence, good heat tolerance and a long flowering period. The new variety is a *Lobularia*, normally produced as an outdoor garden or container plant.

2 Drawing Sheets

Latin name of the genus and species: *Lobularia maritima.*
Variety denomination: 'DLOBU2'.

BACKGROUND OF THE INVENTION

The new *Lobularia* cultivar is a product of a planned breeding program conducted by the inventor, Gavriel Danziger, in Moshav Mishmar Hashiva, Israel. The objective of the breeding program was to produce new *Lobularia* varieties for ornamental commercial applications. The cross resulting in this new variety was made during December of 2009.

The cross resulting in the new variety was made with multiple unpatented, proprietary seedlings, with the actual parent not identifiable. The new variety was discovered in May of 2010 by the inventor in a group of seedlings resulting from the December of 2009 crossing, in a research greenhouse in Moshav Mishmar Hashiva, Israel.

Asexual reproduction of the new cultivar 'DLOBU2' by vegetative cuttings was first performed at a research greenhouse in Moshav Mishmar Hashiva, Israel in May of 2010 and has shown that the unique features of this cultivar are stable and reproduced true to type in successive generations.

SUMMARY OF THE INVENTION

The cultivar 'DLOBU2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DLOBU2' These characteristics in combination distinguish 'DLOBU2' as a new and distinct *Lobularia* cultivar:

1. Good heat tolerance.
2. Long flowering season.
3. Moderate trailing habit.

COMMERCIAL COMPARISON

Plants of the new cultivar 'DLOBU2' are comparable to the variety *Lobularia* 'Inlbusnopr', U.S. Plant Pat. No. 21,594.

The two *Lobularia* varieties are similar in most horticultural characteristics, however, plants of the new variety 'DLOBU2' have more controlled, vigorous growth and a denser, more compact and mounded habit than 'Inlbusnopr'. 'DLOBU2' inflorescence is also denser than this comparator. Additionally, plants of 'DLOBU2' produce smaller leaves and flowers than 'Inlbusnorpr'.

BRIEF DESCRIPTION OF THE PHOTOGRAPHS

Figure 1:
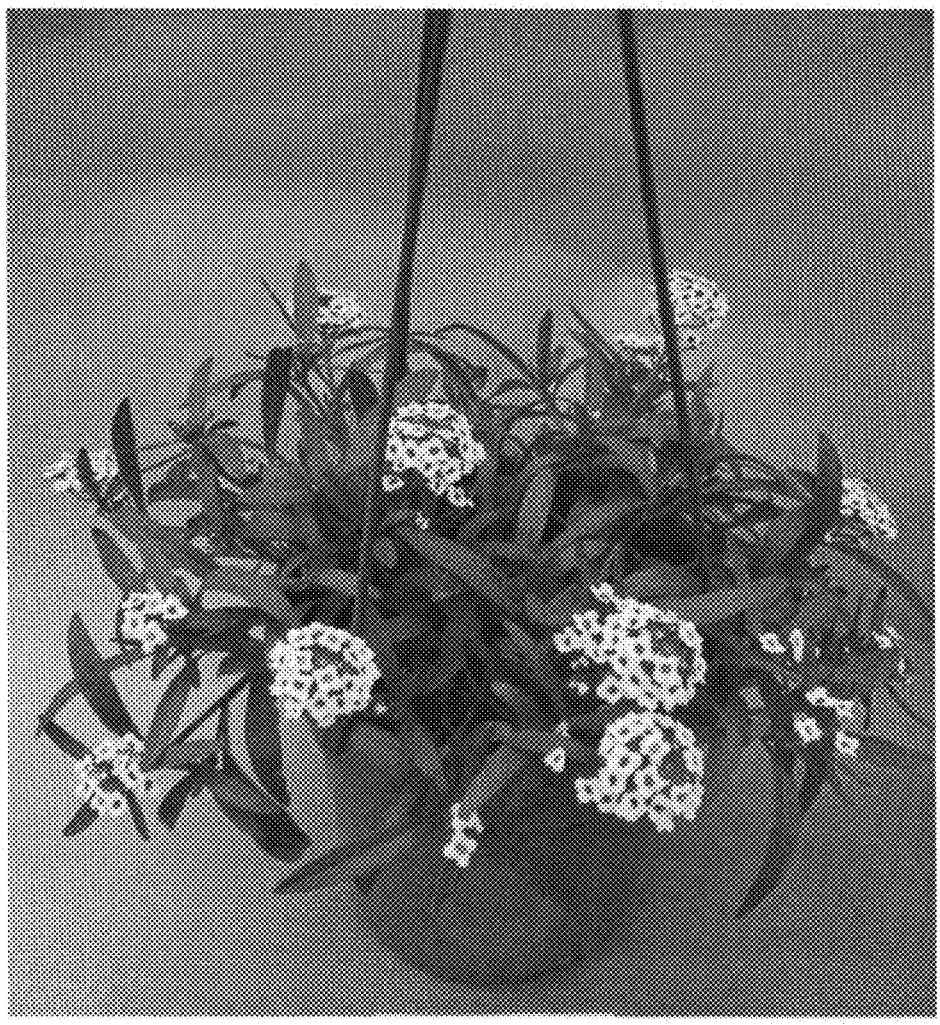

The accompanying photograph in FIG. 1 illustrates in full color a typical plant of 'DLOBU2' grown in a greenhouse, in a 13 cm basket. Age of the plant photographed is approximately 3 months from a rooted cutting.

Figure 2:
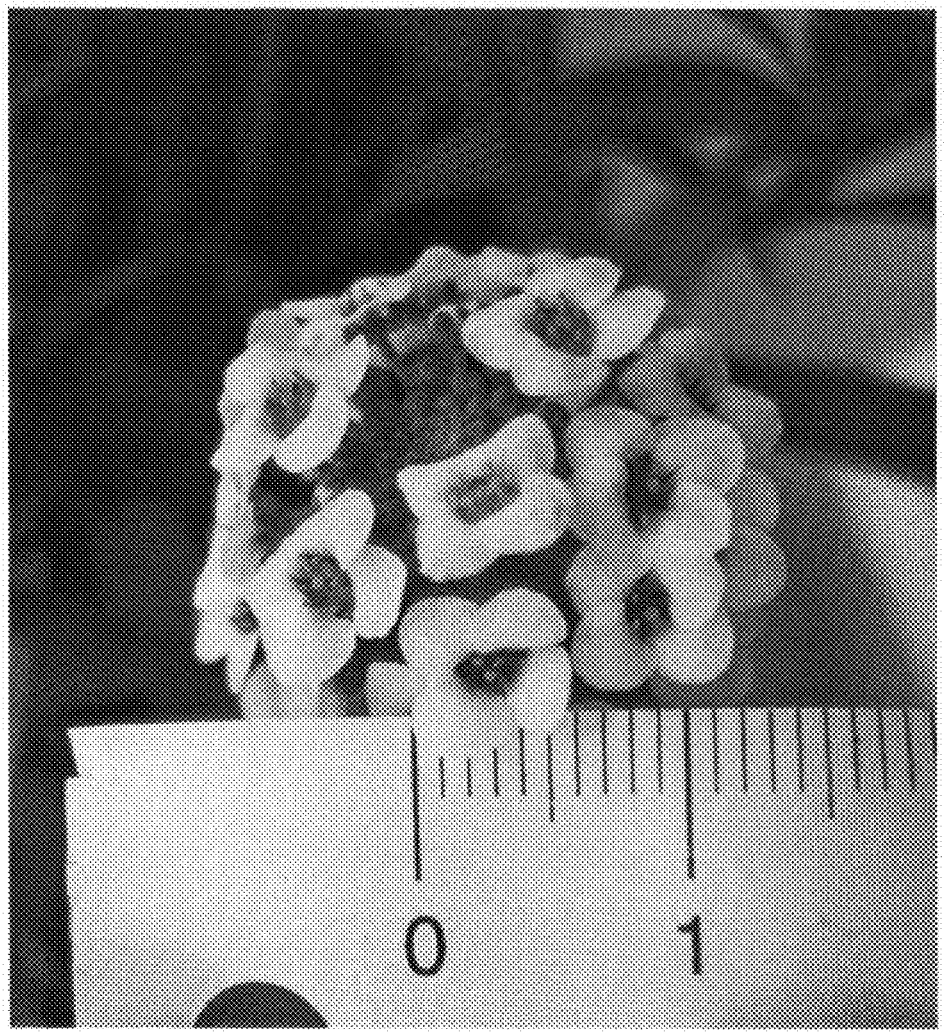

FIG. 2 illustrates in full color a close up of a typical bloom of 'DLOBU2'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DLOBU2' plants grown in a greenhouse, during autumn to spring, in Moshav Mishmar Hashiva, Israel. The growing temperature ranged from 18° C. to 30° C. during the day and from 9° C. to 16° C. during the night. General light conditions are high light levels; 60,000 to 90,000 Lux sunlight. Measurements and numerical values represent averages of typical plant types. Plants are approximately 60 days old from a rooted cutting.

Botanical classification: *Lobularia maritime* 'DLOBU2'.

PROPAGATION

Typical propagation material: Cuttings.
Time to rooting: 14 to 20 days at approximately 16° C.
Root description: Very fine, fibrous.

PLANT

Growth habit: Mounded and trailing habit.
Height: Approximately 15 cm.
Plant spread: Approximately 50 cm.
Growth rate: Medium.
Branching characteristics: Freely branched.
Approximate quantity of lateral branches: Approximately 10 primary lateral branches and numerous secondary and tertiary lateral branches.
Length of lateral branches: Approximately 30 cm.
Diameter of lateral branches: Approximately 3 mm.
Texture of lateral branches: Slightly Pubescent.
Lateral branch shape: Hexagonal in cross section.
Lateral branch strength: Very flexible.
Lateral branch color: Approximately RHS 144A.
Other stem or plant characteristics:
Internode length: Approximately 1.1 cm to 3.5 cm.
Number of leaves per lateral branch: Average 6 leaves.
Age of plant described: Approximately 2 months.

FOLIAGE

Leaf:
*Arrangement.*—Alternate.
*Shape of blade.*—Acute.
*Average length.*—Approximately between 4.5 cm to 7.5 cm (Mature foliage).
*Average width.*—Approximately between 0.5 cm to 1 cm (Mature foliage).
*Apex.*—Acute.
*Base.*—Cuneate.
*Margin.*—Entire.
*Texture of top surface.*—Slightly Pubescent.
*Texture of bottom surface.*—Slightly Pubescent.
*Color.*—Young foliage upper side: Near R.H.S. Green 137B. Young foliage under side: Near R.H.S. Green 137D. Mature foliage upper side: Near R.H.S. Green 137A. Mature foliage under side: Near R.H.S. Green 137B.
*Venation.*—Type: Pinnate. Venation color upper side: Near R.H.S. Green 137A. Venation color under side: Near R.H.S. Green 137B.
Petiole:
*Average length.*—Approximately 5 mm.
*Diameter.*—Approximately 1 mm.
*Color.*—Near R.H.S. Green 137B.
*Texture.*—Glabrous.

FLOWER

Bloom period:
*Natural season.*—Long lasting flowering period. From March through November. In commercial production, flowering begins from a rooted cutting in approximately 4 weeks.
Inflorescence:
*Arrangement.*—Panicle.
*Height.*—Approximately 1.3-1.8 cm.
*Width.*—Approximately 2.2 cm.
*Quantity of flowers per inflorescence.*—Approximately 30.
Bud:
*Bud shape.*—Globose spherical.
*Bud length.*—Approximately 1.5 mm.
*Bud diameter.*—Approximately 1.5 mm.
*Bud color.*—Near R.H.S. Yellow-Green 144A.
Individual flower:
*Type and shape of individual flowers.*—Small rounded, cruciform flowers.
*Quantity of flowers and buds per plant.*—Approximately 40 open flowers per inflorescence.
*Diameter of entire flower.*—Approximately 6.5 mm.
*Depth of flower.*—Approximately 0.5 mm.
*Persistent or self-cleaning.*—Self-cleaning, Not persistent.
*Fragrance.*—Sweet, honey like.
Petals:
*Length of petal.*—Approximately 3 mm.
*Width of petal.*—Approximately 2.5 mm.
*Apex.*—Rounded.
*Base.*—Reniform.
*Shape of petal.*—Oval.
*Petal margin.*—Entire.
*Petal arrangement.*—4 petals fused in a single whorl.
*Petal number.*—4 petals.
*Petal appearance (shiny, matte).*—Matte.
*Petal texture (both upper and lower surfaces).*—Smooth, glabrous.
Color:
*Upper surface at first opening.*—Near RHS White N155D.
*Upper surface at maturity.*—Near RHS White N155D.
*Upper surface at fading.*—Near RHS White 155C.
*Under surface at first opening.*—Near RHS White N155D.
*Under surface at maturity.*—Near RHS White N155D.
*Under surface at fading.*—Near RHS White 155C.

SEPAL

*Number.*—4.
*Sepal arrangement.*—4 sepals in a single whorl.
*Sepal length.*—Approximately 2 mm.
*Sepal width.*—Approximately 1 mm.
*Sepal shape.*—Elliptic.
*Base.*—Truncate.
*Apex shape.*—Acute.
*Margin.*—Entire.
*Color (both upper and lower surfaces).*—Near RHS 144A.
*Texture: Glabrous.*

PEDUNCLE

Length: Approximately 2 cm.
Diameter: Approximately 2 mm.
Strength: Strong.
Color: Near RHS 146B.

PEDICEL

Length: Approximately 1 cm.
Diameter: Approximately 0.5 mm.
Angle: Approximately 75-90 degrees.
Strength: Strong.
Color: Near RHS 146B.

REPRODUCTIVE ORGANS

*Number of pistils per flower.*—1.
*Pistil length.*—Approximately 1.5 mm.
*Stigma shape.*—Rounded to broadly spreading.
*Stigma color.*—Near RHS 144C.
*Style color.*—Near RHS 144B.
*Style length.*—Approximately 0.5 mm.
*Ovary color.*—Near RHS 144B.
*Stamens quantity.*—6.
*Stamen length.*—Less than 1 mm.
*Anther shape.*—Elliptic.
*Anther size.*—Less than 0.5 mm. in length.
*Anther color.*—Near RHS 14A.
*Pollen color.*—Near RHS 14A.
*Pollen quantity.*—Scarce.

OTHER CHARACTERISTICS

Disease resistance: Resistance to pathogens and pests common to *Lobularia* has not been observed.

Drought tolerance and cold tolerance: Plants of the new *Lobularia* have been noted to have good tolerance at temperatures from 1° C. to 35° C. and also tolerate rain and wind conditions.

Fruit/seed production: The fruits and Seeds are elliptical and flat, about 0.2 cm in length. The Color of the mature seed is near RHS Grey-Brown N199B.

What is claimed is:

1. A new and distinct cultivar of *Lobularia* plant named 'DLOBU2' as herein illustrated and described.

* * * * *